US011207354B2

(12) United States Patent
Tanaka et al.

(10) Patent No.: US 11,207,354 B2
(45) Date of Patent: Dec. 28, 2021

(54) SCHWANN CELL DIFFERENTIATION PROMOTING AGENT AND A PERIPHERAL NERVE REGENERATION PROMOTING AGENT

(71) Applicants: OSAKA UNIVERSITY, Suita (JP); NIPPON ZOKI PHARMACEUTICAL CO., LTD., Osaka (JP)

(72) Inventors: Hiroyuki Tanaka, Suita (JP); Tsuyoshi Murase, Suita (JP); Hideki Yoshikawa, Suita (JP); Hiroki Fujisawa, Osaka (JP)

(73) Assignees: OSAKA UNIVERSITY, Osaka (JP); NIPPON ZOKI PHARMACEUTICAL CO., LTD., Osaka (JP)

( * ) Notice: Subject to any disclaimer, the term of this patent is extended or adjusted under 35 U.S.C. 154(b) by 176 days.

(21) Appl. No.: 16/336,236

(22) PCT Filed: Sep. 22, 2017

(86) PCT No.: PCT/JP2017/034374
§ 371 (c)(1),
(2) Date: Mar. 25, 2019

(87) PCT Pub. No.: WO2018/056412
PCT Pub. Date: Mar. 29, 2018

(65) Prior Publication Data
US 2019/0209622 A1 Jul. 11, 2019

(30) Foreign Application Priority Data
Sep. 23, 2016 (JP) .............................. JP2016-186190

(51) Int. Cl.
A61K 35/36 (2015.01)
A61P 25/02 (2006.01)
G01N 33/50 (2006.01)
C12N 7/00 (2006.01)
C12Q 1/6876 (2018.01)

(52) U.S. Cl.
CPC .............. A61K 35/36 (2013.01); A61P 25/02 (2018.01); C12N 7/00 (2013.01); C12Q 1/6876 (2013.01); G01N 33/5023 (2013.01); G01N 33/5058 (2013.01); C12N 2710/24132 (2013.01); C12Q 2600/106 (2013.01); C12Q 2600/158 (2013.01); G01N 2333/07 (2013.01); G01N 2800/7095 (2013.01)

(58) Field of Classification Search
None
See application file for complete search history.

(56) References Cited

U.S. PATENT DOCUMENTS

| | | |
|---|---|---|
| 5,013,558 A | 5/1991 | Konishi |
| 5,560,935 A | 10/1996 | Konishi et al. |
| 6,051,613 A | 4/2000 | Ohno et al. |
| 6,165,515 A | 12/2000 | Matsuyama et al. |
| 7,201,896 B1 | 4/2007 | Revel et al. |
| 2003/0039987 A1 | 2/2003 | Lupski et al. |
| 2006/0051376 A1 | 3/2006 | Nishioka |
| 2006/0263388 A1 | 11/2006 | Nishioka |
| 2007/0218037 A1 | 9/2007 | Nishioka |
| 2008/0057509 A1 | 3/2008 | Lupski et al. |
| 2010/0048408 A1 | 2/2010 | Naiki et al. |
| 2011/0111051 A1 | 5/2011 | Oishi et al. |
| 2013/0028982 A1 | 1/2013 | Tamaki |
| 2013/0122512 A1 | 5/2013 | Mutoh et al. |

FOREIGN PATENT DOCUMENTS

| | | |
|---|---|---|
| EP | 0916344 A2 | 5/1999 |
| EP | 0953352 A1 | 11/1999 |
| EP | 1038529 A2 | 9/2000 |
| EP | 3421989 A1 | 1/2019 |
| EP | 3427726 A1 | 1/2019 |
| JP | S53-101515 A | 9/1978 |
| JP | S55-087724 A | 7/1980 |
| JP | H01-265028 A | 10/1989 |
| JP | H01-319422 A | 12/1989 |
| JP | H02-028119 A | 1/1990 |
| JP | H07-97336 A | 4/1995 |
| JP | H08-291077 A | 11/1996 |
| JP | H10-194978 A | 7/1998 |
| JP | H11-080005 A | 3/1999 |

(Continued)

OTHER PUBLICATIONS

Naiki (Int. J. Immunopharmac. (1991), vol. 13, No. 2/3, pp. 235-243).*
Dec. 12, 2017 International Search Report issued in International Patent Application No. PCT/JP2017/034374.
Houzou MATSUOKA et al. "Neurotropin Promotes Differentiation of Schwann Cells Via Akt, Erk Signal". The Journal of the Japanese Orthopaedic Association, Aug. 2016, vol. 90, No. 8, pp. S1759, 2-pp. 8.
Hiroyuki Tanaka. "The Effect of Neurotropin on Peripheral Nervous System". Journal of the Japan Society of Pain Clinicians, Jun. 2016, vol. 23, No. 3, p. 350.

(Continued)

Primary Examiner — Susan Hoffman
(74) Attorney, Agent, or Firm — Oliff PLC

(57) ABSTRACT

A Schwann cell differentiation promoting agent, a peripheral nerve regeneration promoting agent, or the like contain an extract from inflamed tissues inoculated with vaccinia virus. The extract from inflamed tissues inoculated with vaccinia virus promotes differentiation of Schwann cells and regeneration of a peripheral nerve. Therefore, a preparation containing the extract from inflamed tissues inoculated with vaccinia virus is useful as a Schwann cell differentiation promoting agent, a peripheral nerve regeneration promoting agent, or the like.

8 Claims, No Drawings

Specification includes a Sequence Listing.

(56) References Cited

FOREIGN PATENT DOCUMENTS

| | | |
|---|---|---|
| JP | H11-139977 A | 5/1999 |
| JP | 2000-016942 A | 1/2000 |
| JP | 2000-336034 A | 12/2000 |
| JP | 2003-502382 A | 1/2003 |
| JP | 2004-516832 A | 6/2004 |
| JP | 2004-300146 A | 10/2004 |
| JP | 5288182 B2 | 9/2013 |
| WO | 2000/078331 A2 | 12/2000 |
| WO | 2002/051981 A2 | 7/2002 |
| WO | 2004/039383 A1 | 5/2004 |
| WO | 2009/028605 A1 | 3/2009 |
| WO | 2011/111770 A1 | 9/2011 |
| WO | 2011/162317 A1 | 12/2011 |
| WO | 2012/051173 A2 | 4/2012 |
| WO | 2017/146230 A1 | 8/2017 |
| WO | 2017/154822 A1 | 9/2017 |

OTHER PUBLICATIONS

Katsuya Ishihara et al. "The Receptor for Advanced Glycation End-Products (Rage) Directly Binds to Erk by a D-Domain-Like Docking Site". FEBS Letters, 2003, vol. 550, No. 1/3, pp. 107-113.
Hozo Matsuoka et al. "Neurotropin Accelerates Peripheral Nerve Regeneration by Promoting the Differentiation of Schwann Cells". Journal of Orthopaedic Research, Mar. 2017, vol. 35.
Houzou Matsuoka et al. "Neurotropin Promotes the Differentiation of Schwann Cells and Exerts Peripheral Nerve Regenerating Effect". The Annual Meeting of the Japanese Society for Reconstructive Microsurgery: Program and Abstracts, Oct. 2016, vol. 43, p. 165.
Robert Fledrich et al. "Soluble Neuregulin-1 Modulates Disease Pathogenesis in Rodent Models of Charcot-Marie-Tooth Disease 1A". Nature Medicine, 2014, vol. 20, No. 9, pp. 1055-1061.
The Journal of Japanese Society for Surgery of the Hand, 2013, vol. 30, No. 1, Subject No. 2-5-22.
Dec. 12, 2017 Written Opinion issued in International Patent Application No. PCT/JP2017/034374.

* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Rattus norvegicus

<400> SEQUENCE: 1
aagatcccac agcagcttcc                                             20

<210> SEQ ID NO 2
<211> LENGTH: 20
<212> TYPE: DNA
<213> ORGANISM: Rattus norvegicus

<400> SEQUENCE: 2
taaagaagcg cccgatggag                                             20

<210> SEQ ID NO 3
<211> LENGTH: 20
<212> TYPE: DNA
<213> ORGANISM: Rattus norvegicus

<400> SEQUENCE: 3 gtagggacc ctagctggaa                                              20

<210> SEQ ID NO 4
<211> LENGTH: 20
<212> TYPE: DNA
<213> ORGANISM: Rattus norvegicus

<400> SEQUENCE: 4
tgtccggtgg gtttttgaca                                             20

<210> SEQ ID NO 5
<211> LENGTH: 20
<212> TYPE: DNA
<213> ORGANISM: Rattus norvegicus

<400> SEQUENCE: 5
tgttgctctt cgtctccacc                                             20

<210> SEQ ID NO 6
<211> LENGTH: 20
<212> TYPE: DNA
<213> ORGANISM: Rattus norvegicus

<400> SEQUENCE: 6
gaggagtagc agtgctggac                                             20

<210> SEQ ID NO 7
<211> LENGTH: 20
<212> TYPE: DNA
<213> ORGANISM: Rattus norvegicus

<400> SEQUENCE: 7
tccaagtttg ccatctcgct                                             20

<210> SEQ ID NO 8
<211> LENGTH: 20
<212> TYPE: DNA
<213> ORGANISM: Rattus norvegicus

<400> SEQUENCE: 8
gatggacaga tcgagggcag                                             20

<210> SEQ ID NO 9
<211> LENGTH: 20
<212> TYPE: DNA

```
<213> ORGANISM: Rattus norvegicus

<400> SEQUENCE: 9
gacaactttg gcatcgtgga                                                   20

<210> SEQ ID NO 10
<211> LENGTH: 20
<212> TYPE: DNA
<213> ORGANISM: Rattus norvegicus

<400> SEQUENCE: 10
atgcagggat gatgttctgg                                                   20
```

SCHWANN CELL DIFFERENTIATION PROMOTING AGENT AND A PERIPHERAL NERVE REGENERATION PROMOTING AGENT

TECHNICAL FIELD

The present invention relates to a novel pharmaceutical use or the like of an extract from inflamed tissues inoculated with vaccinia virus (hereinafter, also referred to as "the present extract"). More specifically, the present invention relates to a Schwann cell differentiation promoting agent and a peripheral nerve regeneration promoting agent containing the present extract, or the like.

BACKGROUND ART

Myelin sheaths, which have multilayered structures formed around nerve axons of vertebrates, contribute to effective nerve conduction by saltatory conduction of nerve impulse. The myelin sheaths are formed by Schwann cells in the peripheral nervous system.

Cell bodies of peripheral nerves are present in spinal cord ventral horn in motor nerves, and in dorsal root ganglion (DRG) in sensory nerves. Schwann cells surround an axon protruding from a cell body to form a myelin sheath. When a peripheral nerve is injured, its axon and myelin sheath distal to the injury site are eliminated by phagocytosis (Waller degeneration). The degeneration of axons is accompanied by dedifferentiation of Schwann cells into an undifferentiated state to cause demyelination. Then, during a process of regeneration, the undifferentiated Schwann cells proliferate distal to the injury site to form a scaffold for axonal regeneration. Finally, a regenerated axon extends in a distal direction, which is accompanied by differentiation of Schwann cells surrounding the regenerated axon to form a myelin sheath (remyelination). It is known that Schwann cells play an important role in a process of regeneration of a peripheral nerve as described above.

Although a peripheral nerve has a nerve-regenerative capacity after injury as described above, the restoration ability is not always sufficient for restoring neural function. In a process of regeneration of a peripheral nerve, extension rate of a regenerating nerve is very slow, and the regeneration requires a long period of time, such as several months or a year or longer. Thus, neurons and Schwann cells often degenerate during the period, and the neural function often cannot be restored.

Further, in demyelination condition in a peripheral nerve, it is known that nerve conduction velocity is decreased by demyelination which is caused by Schwann cell dedifferentiation. Thus, it is thought that promoting differentiation and remyelination of undifferentiated Schwann cells is effective for the treatment of peripheral nerve injuries and demyelinating diseases. It should be noted that the term "treatment" used herein includes the meanings of "alleviation", "improvement", "prevention of progression", and the like.

It is known that an extract from inflamed tissues inoculated with vaccinia virus (the present extract), which is contained in a Schwann cell differentiation promoting agent or a peripheral nerve regeneration promoting agent according to the present invention, or a preparation containing the extract exerts a wide variety of actions and effects, such as an analgesic action, sedation, an antistress action, and an antiallergic action (see Patent Document 1); an immunostimulation action, an anticancer action, and a hepatic cirrhosis inhibitory action (see Patent Document 2); a therapeutic effect on idiopathic thrombocytopenic purpura (see Patent Document 3); therapeutic effects on postherpetic neuralgia, cerebral edema, dementia, spinocerebellar degeneration, and the like (see Patent Document 4); therapeutic effects on Raynaud's syndrome, a diabetic neurological disorder, a sequela of subacute myelo-optico-neuropathy, and the like (see Patent Document 5); a kallikrein-production-inhibitory action and a peripheral circulatory disturbance ameliorating action (see Patent Document 6); a bone atrophy ameliorating action (see Patent Document 7); a nitric oxide-production-inhibitory action effective for the treatment of sepsis or endotoxic shock (see Patent Document 8); a therapeutic effect on osteoporosis (see Patent Document 9); AIDS treatment effects based on a Nef-activity-inhibitory action or a chemokine-production-inhibitory action (see Patent Documents 10 and 11); therapeutic effects on ischemic diseases such as cerebral infarction (see Patent Document 12); a therapeutic effect on fibromyalgia (see Patent Document 13); a therapeutic effect on an infectious disease (see Patent Document 14); an action of preventing or alleviating a peripheral nerve disorder caused by an anticancer agent (see Patent Document 15); therapeutic effects on chronic prostatitis, interstitial cystitis and/or dysuria (see Patent Document 16); a neurotrophic factor (e.g., BDNF)-production promoting action (see Patent Document 17); and collagen and proteoglycan synthesis promoting actions on chondrocytes (see Patent Document 18). In addition, a Schwann cell proliferation promoting action has recently been reported (see Non-Patent Document 1). However, it has not been known that the present extract or a preparation containing the extract has a Schwann cell differentiation promoting action or a peripheral nerve regeneration promoting action.

PRIOR ART DOCUMENTS

Patent Documents

[Patent Document 1] Japanese Patent Laid-Open No. Sho-53-101515
[Patent Document 2] Japanese Patent Laid-Open No. Sho-55-87724
[Patent Document 3] Japanese Patent Laid-Open No. Hei-1-265028
[Patent Document 4] Japanese Patent Laid-Open No. Hei-1-319422
[Patent Document 5] Japanese Patent Laid-Open No. Hei-2-28119
[Patent Document 6] Japanese Patent Laid-Open No. Hei-7-97336
[Patent Document 7] Japanese Patent Laid-Open No. Hei-8-291077
[Patent Document 8] Japanese Patent Laid-Open No. Hei-10-194978
[Patent Document 9] Japanese Patent Laid-Open No. Hei-11-80005
[Patent Document 10] Japanese Patent Laid-Open No. Hei-11-139977
[Patent Document 11] Japanese Patent Laid-Open No. 2000-336036
[Patent Document 12] Japanese Patent Laid-Open No. 2000-16942
[Patent Document 13] International Publication No. WO 2004/039383
[Patent Document 14] Japanese Patent Laid-Open No. 2004-300146

[Patent Document 15] International Publication No. WO2009/028605
[Patent Document 16] International Publication No. WO2011/111770
[Patent Document 17] International Publication No. WO2011/162317
[Patent Document 18] International Publication No. WO2012/051173

Non-Patent Documents

[Non-Patent Document 1] The Journal of Japanese Society for Surgery of the Hand, Vol. 30, No. 1, Subject No. 2-5-22, 2013

SUMMARY OF THE INVENTION

Problem to be Solved by the Invention

The present invention provides a Schwann cell differentiation promoting agent containing the present extract, a peripheral nerve regeneration promoting agent containing the present extract, and the like.

Means for Solving the Problems

The present inventors have made a diligent study on a pharmacological treatment of a peripheral nerve injury for which an effective therapy is required. As a result, the present inventors have found that the present extract has an excellent Schwann cell differentiation promoting action and an excellent peripheral nerve regeneration promoting action, and have accomplished the present invention.

Advantages of the Invention

The present extract has an excellent pharmacological action to promote differentiation of Schwann cells and regeneration of a peripheral nerve. In addition, since a preparation containing the present extract has been used for a long time as a highly safe drug with little problem such as a side effect, the present invention is exceptionally useful.

MODE FOR CARRYING OUT THE INVENTION

The present extract is an extract containing a non-protein active substance extracted and separated from inflamed tissues of an animal having developed pox by being inoculated with vaccinia virus. The present extract is in liquid when it is extracted; however, the present extract may be made solid by drying. The present preparation is very useful as pharmaceuticals. One specific product that is manufactured and sold in Japan by the applicant as the present preparation is "Preparation containing an extract from inflamed rabbit skin inoculated with vaccinia virus" (trade name: NEUROTROPIN [registered trademark]) (hereinafter, referred to as "NEUROTROPIN"). NEUROTROPIN includes injections and tablets, both of which are ethical drugs.

Indications of NEUROTROPIN injection are "low back pain, cervicobrachial syndrome, symptomatic neuralgia, itchiness accompanied by skin diseases (eczema, dermatitis, urticaria), allergic rhinitis and sequelae of subacute myelo-optico-neuropathy (SMON) such as coldness, paresthesia and pain". Indications of NEUROTROPIN tablet are "postherpetic neuralgia, low back pain, cervicobrachial syndrome, periarthritis scapulohumeralis and osteoarthritis".

Present preparation has been created by the applicant and developed as a drug, and has been appreciated for its excellent advantage for efficacy and safety, sold for many years and established a firm position in the Japanese pharmaceutical market.

The extract from inflamed tissues inoculated with vaccinia virus used in the present invention can be obtained by the following manner: inflamed tissues inflamed by the inoculation with vaccinia virus is crushed; an extraction solvent is added to remove the tissue fragments; then deproteinization is carried out; the deproteinized solution is adsorbed onto an adsorbent; and then the active ingredient is eluted. For example, according to the following process.

(A) Inflamed skin tissues of rabbits, mice or the like by the inoculation with vaccinia virus are collected, and the inflamed tissues are crushed. To the crushed tissue an extraction solvent such as water, phenolated water, physiological saline or phenol-added glycerin water is added. Then, the mixture is filtered or centrifuged to obtain an extraction liquid (filtrate or supernatant).

(B) The pH of the extraction liquid is adjusted to be acidic and the liquid is heated for deproteinization. Then, the deproteinized solution is adjusted to be alkaline, heated, and then filtered or centrifuged.

(C) The obtained filtrate or supernatant is made acidic and adsorbed onto an adsorbent such as activated carbon or kaolin.

(D) To the adsorbent, an extraction solvent such as water is added, the pH is adjusted to alkaline, and the adsorbed component is eluted to obtain the extract from inflamed tissues inoculated with vaccinia virus. Subsequently, as desired, the eluate may be evaporated to dryness under reduced pressure or freeze-dried to give a dried material.

As for animals in order to obtain the inflamed tissues by the inoculation of vaccinia virus, various animals that is infected with vaccinia virus such as rabbits, cows, horses, sheep, goats, monkeys, rats or mice can be used, and preferred inflamed tissues are inflamed skin tissues of rabbits. With regard to a rabbit, any rabbit may be used so far as it belongs to Lagomorpha. Examples thereof include *Oryctolagus cuniculus*, domestic rabbit (domesticated *Oryctolagus cuniculus*), hare (Japanese hare), mouse hare and snowshoe hare. Among them, it is appropriate to use domestic rabbit. In Japan, there is family rabbit called "Kato" which has been bred since old time and frequently used as livestock or experimental animal and it is another name of domestic rabbit. There are many breeds in domestic rabbit and the breeds being called Japanese white and New Zealand white are advantageously used.

Vaccinia virus used herein may be in any strain. Examples thereof include Lister strain, Dairen strain, Ikeda strain, EM-63 strain and New York City Board of Health strain.

As to basic extracting steps (A) to (D) of the above-described for the present extract can be carried out in more detail, the following steps are used for example.

About Step (A):

The inflamed skin tissues of rabbits by the intradermal inoculation of vaccinia virus are collected. The collected skin tissues are washed and disinfected using a phenol solution, etc. This inflamed skin tissues are crushed and an extraction solvent in 1- to 5-fold thereof by volume is added thereto. Here, the term "crush" means to finely break down into minces using a mincing machine or the like. As to the extraction solvent, there may be used distilled water, physiological saline, weakly acidic to weakly basic buffer, etc. and bactericidal/antiseptic agent such as phenol, stabilizer such as glycerin, salts such as sodium chloride, potassium chloride or magnesium chloride, etc. may be appropriately added thereto. At that time, it is also possible that the cell tissue is destroyed by a treatment such as freezing/melting, ultrasonic wave, cell membrane dissolving enzyme or surfactant so as to make the extraction easier. The resulting suspension is allowed to stand for 5 to 12 days. During that period, the suspension may be heated at 30 to 45° C. with or without appropriate stirring. The resulting liquid is subjected to a treatment for separating into solid and liquid (filtered or centrifuged, etc.) to remove the tissue fragments whereupon a crude extract (filtrate or supernatant) is obtained.

About Step (B)

The crude extract obtained in step (A) is subjected to a deproteinizing treatment. The deproteinization may be carried out by a known method which has been usually conducted and a method such as heating treatment, treatment with a protein denaturant (such as acid, base, urea, guanidine or an organic solvent including acetone), isoelectric precipitation or salting-out may be applied. After that, a common method for the removal of insoluble matters such as filtration using filter paper (such as cellulose or nitrocellulose), glass filter, Celite or Seitz filter, ultrafiltration or centrifugation is conducted to give a filtrate or a supernatant wherefrom the separated insoluble protein is removed.

About Step (C)

The filtrate or supernatant obtained in step (B) is adjusted to acidic or, preferably, to pH 3.5 to 5.5 to conduct an operation of adsorbing with an adsorbent. Examples of the usable adsorbent include activated carbon and kaolin. An adsorbent is added to the extract followed by stirring or the extract is passed through a column filled with an adsorbent so that the active ingredient can be adsorbed with the adsorbent. When an adsorbent is added to the extract, the adsorbent with which the active ingredient is adsorbed can be obtained by means of filtration, centrifugation, etc. to remove the solution.

About Step (D)

For elution (desorption) of the active ingredient from the adsorbent obtained in step (C), an elution solvent is added to said adsorbent and adjusted to basic or, preferably, to pH 9 to 12, elution is conducted at room temperature or with suitable heating, or with stirring, and then the adsorbent is removed by a common method such as filtration or centrifugation. As to the extraction solvent used therefore, there may be used a basic solvent such as water, methanol, ethanol, isopropanol or the like adjusted to basic pH or an appropriate mixed solvent thereof and preferably, water adjusted to pH 9 to 12 may be used. Amount of the extracting solvent may be appropriately set. In order to use the eluate obtained as such as a drug substance, the pH is appropriately adjusted to nearly neutral or the like whereby an extract from inflamed skins of rabbits inoculated with vaccinia virus (the present extract) can be finally obtained.

Since the present extract is liquid at the stage of being prepared, it is also possible that said extract is appropriately concentrated or diluted to make into a desired concentration. When a preparation is manufactured from the present extract, it is preferred to apply a sterilizing treatment with heating. For making into an injectable preparation, it is possible to add sodium chloride or the like so as to prepare a solution being isotonic to physiological saline. It is also possible that the present extract is administered in a liquid or gel state. Furthermore, the present extract may be subjected to an appropriate operation such as concentration to dryness to prepare a solid preparation for oral administration such as a tablet. Specific methods for the manufacture of solid preparation for oral administration from the present extract are disclosed in the specifications of Japanese Patent Nos. 3,818,657 and 4,883,798. The present preparation includes an injectable preparation, a solid preparation for oral administration, etc. prepared as such. In addition, the present preparation may be topically applied where to make Muse cells migrate by use of a catheter.

Hereinafter, examples of methods for producing the present extract as well as a novel pharmacological action of and results of pharmacological tests regarding a Schwann cell differentiation promoting action and a peripheral nerve regeneration promoting action of the present extract are described. The present invention is not intended to be limited to the descriptions in Examples.

EXAMPLES

Example 1 (Manufacture of the Present Extract)

Skins of healthy adult rabbits were inoculated with vaccinia virus intradermally and the inflamed skins were cut and collected. The collected skins were washed and disinfected by a phenol solution, an excessive phenol solution was removed and the residue was crushed. A phenol solution was added thereto and mixed therewith and the mixture was allowed to stand for 3 to 7 days, and further heated at 35 to 40° C. together with stirring for 3 to 4 days. After that, an extracted solution obtained by a solid-liquid separation was adjusted to pH 4.5 to 5.2 with hydrochloric acid, heated at 90 to 100° C. for 30 minutes and filtered to remove protein. The filtrate was adjusted to pH 9.0 to 9.5 with sodium hydroxide, heated at 90 to 100° C. for 15 minutes and subjected to a solid-liquid separation.

The resulting deproteinized solution was adjusted to pH 4.0 to 4.3 with hydrochloric acid, activated carbon in an amount of 2% to the mass of the deproteinized solution was added thereto and the mixture was stirred for 2 hours and subjected to the solid-liquid separation. Water was added to the collected activated carbon followed by adjusting to pH 9.5 to 10 with sodium hydroxide and the mixture was stirred at 60° C. for 90 to 100 minutes and centrifuged to give a supernatant. Water was added again to the activated carbon precipitated upon the centrifugation followed by adjusting to pH 10.5 to 11 with sodium hydroxide and the mixture was stirred at 60° C. for 90 to 100 minutes and centrifuged to give a supernatant. Both supernatants were combined and neutralized with hydrochloric acid to give the present extract.

Example 2 (Test Method and Test Result)

Next, test methods and test results of pharmacological tests showing the Schwann cell differentiation promoting action and the peripheral nerve regeneration promoting action of the present extract obtained in Example 1 are shown.

Cells and Reagents

In Test examples 1, 2, and 4, Schwann cells prepared by the following procedure were used.

Primary culture of Schwann cells was prepared by extirpation of sciatic nerves from 1 to 3 day-old Wistar rats. After 3 to 8 passages of the culture, the resulting cells were used for the experiments. For culturing the cells, Dulbecco's Modified Eagle's Medium (DMEM) supplemented with 3% FBS, 20 ng/ml neuregulin, and 3 µM forskolin was used.

In Test example 3, Schwann cells prepared by the following procedure were used.

Primary culture of Schwann cells was prepared by extirpation of sciatic nerves from 1 to 5 day-old Wistar rats. After 3 to 10 passages of the culture, the resulting cells were used for the experiment. For culturing the cells, DMEM supplemented with 3% FBS, 20 ng/ml neuregulin, and 300 nM forskolin was used. Using Schwann cells thus prepared, effects of the present extract on intracellular signaling in Schwann cells, expression of myelin sheath-associated proteins, and myelination of axons were investigated.

Major structural proteins of myelin sheaths are myelin sheath-associated proteins such as Myelin Basic Protein (hereinafter, referred to as "MBP"), Myelin Protein Zero (hereinafter referred to as "P0"), and the like. In general, expression of the myelin sheath-associated proteins is considered as an index of differentiation of oligodendrocyte (cells forming myelin sheaths in the central nervous system) and Schwann cells. That is, when there is a myelin sheath-associated protein-expression promoting action, it is thought that there are oligodendrocyte and Schwann cell differentiation promoting actions.

Statistical Analysis

In Test examples 1, 2, and 4 to 7, statistical analysis was performed by Tukey-Kramer HSD test using JMP software version 11 (SAS Institute).

In Test example 3, statistical analysis was performed by Bartlett's test for comparison among multiple groups, by Dunnett's multiple comparison test in the case of equal variance, or by Steel's multiple comparison test in the case of unequal variance using SAS System Version 9.1.3 (SAS Institute).

Test Example 1: Evaluation of Effect of the Present Extract on Intracellular Signaling in Schwann Cells (Growth Medium)

Schwann cells were inoculated into a medium of DMEM supplemented with 3% fetal bovine serum (FBS), 20 ng/ml neuregulin, and 3 µM forskolin in a 35-mm poly-L-lysine coated dish at a density of $2 \times 10^4$ cells/cm$^2$. After 24-hour culture, the present extract was added, and cytolysate was prepared using Kaplan buffer (50 mM Tris, pH 7.4, 150 mM NaCl, 10% glycerol, and 1% NP40). The cytolysate was subjected to electrophoresis by 12% SDS-PAGE, and then transferred to polyvinylidene difluoride membranes. The membranes were blocked with 5% skim milk, and reacted overnight at 4° C. with an anti-phospho-AKT antibody (1:1000; Cell Signaling Technology, Inc.), an anti-AKT antibody (1:1000; Cell Signaling Technology, Inc.), an anti-phospho-p44/42 MAPK antibody (1:1000; Cell Signaling Technology, Inc.), an anti-p44/42 MAPK antibody (1:1000; Cell Signaling Technology, Inc.), an anti-phospho-p38 antibody (1:1000; Cell Signaling Technology, Inc.), and an anti-p38 antibody (1:1000; Cell Signaling Technology, Inc.) as primary antibodies. The reacted membranes were reacted for 1 hour with a HRP-labeled anti-rabbit IgG antibody (1:1000; Cell Signaling Technology, Inc.) as a secondary antibody, and then reacted with an ECL reagent (GE Healthcare) to detect bands using MF-ChemiBIS 3.2 (DNR Bio-Imaging Systems Ltd.). Staining intensity of each band was measured to calculate a ratio of phospho-AKT (pAKT) to AKT, a ratio of phospho-ERK (pERK) to ERK, and a ratio of phospho-p38 (p-p38) to p38 (mean±standard error). Examples of results of the above test are shown in Table 1, Table 2, and Table 3.

TABLE 1

| | The Ratio of pAKT to AKT |
|---|---|
| Control | 1.00 ± 0.06 |
| Present Extract 0.1 mNU/mL | 1.88 ± 0.06* |
| Present Extract 0.2 mNU/mL | 1.74 ± 0.05** |
| Present Extract 0.5 mNU/mL | 2.03 ± 0.05* |

*$p < 0.05$ vs Control,
**$p < 0.01$ vs Control

TABLE 2

| | The Ratio of pERK to ERK |
|---|---|
| Control | 1.00 ± 0.04 |
| Present Extract 0.1 mNU/mL | 0.84 ± 0.06 |
| Present Extract 0.2 mNU/mL | 0.47 ± 0.14* |
| Present Extract 0.5 mNU/mL | 0.33 ± 0.11** |

*$p < 0.05$ vs Control,
**$p < 0.01$ vs Control

TABLE 3

| | The Ratio of p-p38 to p38 |
|---|---|
| Control | 1.00 ± 0.04 |
| Present Extract 0.1 mNU/mL | 0.84 ± 0.06 |
| Present Extract 0.2 mNU/mL | 0.47 ± 0.14* |
| Present Extract 0.5 mNU/mL | 0.33 ± 0.11** |

*$p < 0.05$ vs Control,
**$p < 0.01$ vs Control

In the growth medium, in the present extract group, phosphorylation of AKT increased significantly (Table 1), phosphorylation of ERK decreased significantly (Table 2), and phosphorylation of p38 decreased significantly (Table 3) as compared with the control group. Thus, it was confirmed that the present extract promotes differentiation signals of undifferentiated Schwann cells.

Test Example 2: Evaluation of Effect of the Present Extract on Intracellular Signaling in Schwann Cells (Differentiation Medium)

Schwann cells were inoculated into a medium of DMEM supplemented with 3% fetal bovine serum (FBS), 20 ng/ml neuregulin, and 3 µM forskolin in a 35-mm poly-L-lysine coated dish at a density of $2 \times 10^4$ cells/cm$^2$. After 24-hour culture, 1 mM of cAMP was added to the culture to induce differentiation, and the present extract was simultaneously added thereto. Cytolysate was prepared using Kaplan buffer (50 mM Tris, pH 7.4, 150 mM NaCl, 10% glycerol, and 1% NP40). The cytolysate was subjected to electrophoresis by 12% SDS-PAGE, and then transferred to polyvinylidene difluoride membranes. The membranes were blocked with 5% skim milk, and reacted overnight at 4° C. with an anti-phospho-AKT antibody (1:1000; Cell Signaling Technology, Inc.), an anti-AKT antibody (1:1000; Cell Signaling Technology, Inc.), an anti-phospho-p44/42 MAPK antibody (1:1000; Cell Signaling Technology, Inc.), and an anti-p44/42 MAPK antibody (1:1000; Cell Signaling Technology, Inc.) as primary antibodies. The reacted membranes were reacted for 1 hour with a HRP-labeled anti-rabbit IgG antibody (1:1000; Cell Signaling Technology, Inc.) as a secondary antibody, and then reacted with an ECL reagent (GE Healthcare) to detect bands using MF-ChemiBIS 3.2 (DNR Bio-Imaging Systems Ltd.). Staining intensity of each band was measured to calculate a ratio of pAKT to AKT and a ratio of pERK to ERK (mean±standard error). Examples of results of the above test are shown in Table 4 and Table 5.

TABLE 4

|  | The Ratio of pAKT to AKT |
| --- | --- |
| Control | 1.00 ± 0.04 |
| cAMP | 1.91 ± 0.07* |
| cAMP Present Extract | 7.00 ± 0.16# |

*$p < 0.05$ vs Control,
$p < 0.05$ vs cAMP

TABLE 5

|  | The Ratio of pERK to ERK |
| --- | --- |
| Control | 1.00 ± 0.08 |
| cAMP | 0.80 ± 0.15 |
| cAMP Present Extract | 0.28 ± 0.05# |

$p < 0.05$ vs cAMP

In differentiation medium, in the present extract group, phosphorylation of AKT increased significantly (Table 4) and phosphorylation of ERK decreased significantly (Table 5) as compared with the cAMP group. Thus, it was confirmed that the present extract further promotes differentiation of differentiation-induced Schwann cells.

Test Example 3: Evaluation of Effect of the Present Extract on Expression of Myelin Sheath-Associated Protein of Schwann Cells (Western Blotting)

Schwann cells were inoculated into a DMEM supplemented with 3% fetal bovine serum (FBS), 20 ng/ml neuregulin, and 3 μM forskolin in a 35-mm poly-L-lysine coated dish at a density of $2 \times 10^4$ cells/cm². After 24-hour culture, 1 mM of cAMP was added to the culture to induce differentiation, and the present extract was simultaneously added thereto. After 72 hours, cytolysate was prepared using Kaplan buffer (50 mM Tris, pH 7.4, 150 mM NaCl, 10% glycerol, and 1% NP40). The cytolysate was subjected to electrophoresis by 12% SDS-PAGE, and then transferred to polyvinylidene difluoride membranes. The membranes were blocked with 5% skim milk, and reacted overnight at 4° C. with an anti-MBP antibody (1:1000; Sigma-Aldrich Co. LLC.) and an anti-P0 antibody (1:1000; Abcam), which indicate myelin sheath proteins, as primary antibodies. The reacted membranes were reacted for 1 hour with a HRP-labeled anti-rabbit IgG antibody (1:1000; Cell Signaling Technology, Inc.) as a secondary antibody, and then reacted with an ECL reagent (GE Healthcare) to detect bands using MF-ChemiBIS 3.2 (DNR Bio-Imaging Systems Ltd.). Staining intensity of each band was measured to calculate ratios of MBP and P0 to GAPDH (mean±standard error). Examples of results of the above test are shown in Table 6 and Table 7.

TABLE 6

|  | The Ratio of MBP to GAPDH |
| --- | --- |
| Control | 1.00 ± 0.03 |
| Present Extrac | 1.37 ± 0.03 |
| cAMP | 1.73 ± 0.03 |
| cAMP Present Extract | 2.64 ± 0.02** |

**$p < 0.01$ vs cAMP

TABLE 7

|  | The Ratio of P0 to GAPDH |
| --- | --- |
| Control | 1.00 ± 0.01 |
| Present Extrac | 2.06 ± 0.06# |
| cAMP | 2.07 ± 0.03 |
| cAMP Present Extract | 3.13 ± 0.04** |

$p < 0.05$ vs Control,
**$p < 0.01$ vs cAMP

As compared with groups in which cAMP was added solely, expression of such proteins as MBP (Table 6) and P0 (Table 7) was significantly increased by adding the present extract in addition to cAMP.

Test Example 4: Evaluation of Effect of the Present Extract on mRNA Expression of Myelin Sheath-Associated Protein of Schwann Cells (Real-Time PCR)

Schwann cells were cultured for 24 hours in a medium of DMEM supplemented with 3% FBS, 20 ng/ml neuregulin, and 300 nM forskolin, and further cultured for 24 hours in a medium without neuregulin and forskolin. Then, neuregulin, forskolin, and the present extract were added to the culture, and the cells were cultured for 8 hours and then collected. RNAs were purified from the collected cells using RNeasy mini kit (QIAGEN), and cDNAs were synthesized by reverse transcription. Gene levels of myelin sheath-associated proteins, expression of which is increased by differentiation of Schwann cells, were measured by real-time PCR using specific primer pairs shown in Table 8. Ratios in each group relative to the amount of mRNA expressed in the control as 1 were calculated (mean±standard error). Examples of results of the above test are shown in Table 9 to Table 12.

TABLE 8

|  | sense | SEQ ID NO | antisense | SEQ ID NO |
| --- | --- | --- | --- | --- |
| MBP | AAGATCCCACAGCAGCTTCG | SEQ ID NO: 1 | TAAAGAAGCGCCCGATGGAG | SEQ ID NO: 2 |
| P0 | GTAGGGGACCCTAGCTGGAA | SEQ ID NO: 3 | TGTCCGGTGGGTTTTTGACA | SEQ ID NO: 4 |
| PMP22 | TGTTGCTCTTCGTCTCCACC | SEQ ID NO: 5 | GAGGAGTAGCAGTGCTGGAC | SEQ ID NO: 6 |
| Periaxin | TCCAAGTTTGCCATCTCGCT | SEQ ID NO: 7 | GATGGACAGATCGAGGGCAG | SEQ ID NO: 8 |
| GAPDH | GACAACTTTGGCATCGTGGA | SEQ ID NO: 9 | ATGCAGGGATGATGTTCTGG | SEQ ID NO: 10 |

TABLE 9

| | Ratio of each group to control (as 1) in MBP expression |
|---|---|
| Control | 1.00 ± 0.04 |
| Forskolin | 0.45 ± 0.06# |
| Neuregulin | |
| Forskolin | 0.59 ± 0.03 |
| Neuregulin | |
| Present Extract 10 mNU/mL | |
| Forskolin | 0.99 ± 0.03* |
| Neuregulin | |
| Present Extract 10 mNU/mL | |

$p < 0.05$ vs Control,
*$p < 0.05$ vs Forskolin and Neuregulin

TABLE 10

| | Ratio of each group to control (as 1) in P0 expression |
|---|---|
| Control | 1.00 ± 0.07 |
| Forskolin | 0.91 ± 0.05 |
| Neuregulin | |
| Forskolin | 0.94 ± 0.06 |
| Neuregulin | |
| Present Extract 10 mNU/mL | |
| Forskolin | 1.48 ± 0.03* |
| Neuregulin | |
| Present Extract 10 mNU/mL | |

*$p < 0.05$ vs Forskolin and Neuregulin

TABLE 11

| | Ratio of each group to control (as 1) in PMP22 expression |
|---|---|
| Control | 1.00 ± 0.04 |
| Forskolin | 0.75 ± 0.02# |
| Neuregulin | |
| Forskolin | 0.97 ± 0.05 |
| Neuregulin | |
| Present Extract 10 mNU/mL | |
| Forskolin | 1.74 ± 0.03* |
| Neuregulin | |
| Present Extract 10 mNU/mL | |

$p < 0.05$ vs Control,
*$p < 0.05$ vs Forskolin and Neuregulin

TABLE 12

| | Ratio of each group to control (as 1) in periaxin expression |
|---|---|
| Control | 1.00 ± 0.13 |
| Forskolin | 1.02 ± 0.04 |
| Neuregulin | |
| Forskolin | 0.85 ± 0.07 |
| Neuregulin | |
| Present Extract 10 mNU/mL | |
| Forskolin | 1.40 ± 0.09* |
| Neuregulin | |
| Present Extract 10 mNU/mL | |

*$p < 0.05$ vs Forskolin and Neuregulin

As compared with forskolin- and neuregulin-addition groups, mRNA expression of MBP (Table 9), P0 (Table 10), PMP22 (Table 11), and periaxin (Table 12) were significantly enhanced by further adding 100 mNU/mL of the present extract.

Test Example 5: Evaluation of Effect of the Present Extract on Differentiation of Schwann Cells DRG neurons were obtained from 15-day embryos of Wistar rats, and inoculated into a Neurobasal medium containing 2% B27 nutrient supplement, 0.2 mmol/L L-glutamine, 1% Penicillin-Streptomycin, and 50 ng/mL nerve growth factor in an 8-well slide chamber coated with poly-L-lysine and laminin at a density of $4 \times 10^4$ cells/well. At 7 days after the inoculation, differentiation was induced by adding 50 g/ml ascorbic acid, and the present extract was added. At 14 days and 21 days after the induction of differentiation, immunofluorescence staining was conducted. The cells were reacted overnight at 4° C. with an anti-MBP antibody (Calbiochem) and an anti-neurofilament 200 antibody (Sigma-Aldrich Co. LLC.) as primary antibodies. The reacted cells were reacted for 1 hour with Alexa 594-labeled goat anti-rabbit IgG antibody (1:1000; Molecular Probes Inc.) and Alexa 488-labeled goat anti-mouse IgG antibody (1:1000; Molecular Probes Inc.) as secondary antibodies. After the secondary antibody reaction, the cells were reacted with a mounting medium (product name: Perma fluor [registered trademark]; Thermo Fisher Scientific) containing DAPI (4'-6-diamidinophenyl-2-indole; Wako Pure Chemical Corporation) to evaluate nuclei. Using NIS Elements BR software (Nikon Corporation), length and width of a MBP-positive region were evaluated (mean±standard error). Examples of results of the above test are shown in Table 13 and Table 14.

TABLE 13

| | Length of a MBP-positive region (μm) | |
|---|---|---|
| | 14 days after the induction of differentiation | 21 days after the induction of differentiation |
| Control | 45.2 ± 2.30 | 50.7 ± 0.64 |
| Present Extract | 51.7 ± 1.25* | 60.7 ± 2.54** |

*$p < 0.05$ vs Control (14 days after the induction of differentiation),
**$p < 0.01$ vs Control (21 days after the induction of differentiation)

TABLE 14

| | Width of a MBP-positive region (μm²) | |
|---|---|---|
| | 14 days after the induction of differentiation | 21 days after the induction of differentiation |
| Control | 2288 ± 92.8 | 3569 ± 111 |
| Present Extract | 3741 ± 132** | 5171 ± 81.1*** |

**$p < 0.01$ vs Control (14 days after the induction of differentiation),
***$p < 0.001$ vs Control (21 days after the induction of differentiation)

As compared with the control group, at 14 days and 21 days after the induction of differentiation, length (Table 13) and area (Table 14) of the MBP-positive region increased significantly in the present extract group, and thus the promotion of differentiation of Schwann cells was confirmed.

Test Example 6: Evaluation in Sciatic Nerve Crush Injury Model

Using a sciatic nerve crush injury model, effects of the present extract on remyelination after nerve injury were investigated. The present extract was continuously administered to rats by using an osmotic pump, and the immunohistological evaluation was conducted.

(1) Preparation of Sciatic Nerve Crush Model Rats and Administration of Present Extract An osmotic pump (product name: alzet [registered trademark], model: 2ML2, product of DURECT) was filled with saline, or the present extract, and stood still overnight in saline at 37° C. Male Wistar rats aged 6 weeks were deeply anesthetized using intraperitoneal administration of a mixed anesthetic of midazolam (2 mg/kg), butorphanol (2.5 mg/kg), and medetomidine (0.15 mg/kg). The left sciatic nerve of rats was exposed and a crush injury was applied with a pair of forceps at 5 mm distal from the sciatic notch. The crushing time was 10 seconds, the number of crushing operations was three, and the interval of the crushing operations was 10 seconds. The fascia and skin were sutured with a 4-0 nylon suture. Either a saline-filled osmotic pump or a present extract-filled osmotic pump (12 NU/kg/day) was placed subcutaneously in the back of rats. Experimental rats were divided into the following two groups.

(1) Control group: sciatic nerve crush injury is applied, and saline is systemically administered (2) Present extract administration group: sciatic nerve crush injury is applied, and the present extract is systemically administered The osmotic pump was indwelled for 2 weeks, and the osmotic pump was replaced, and further indwelled for 2 weeks, and thus the present extract or saline was continuously administered for 4 weeks.

(2) Immunohistological Evaluation

Rats after a lapse of 4 weeks from the operation were sedated with an anesthetic, and sciatic nerves were sampled. The sciatic nerves were fixed in 4% paraformaldehyde for 24 hours at room temperature, then dipped in 20% sucrose liquid, embedded in a Tissue-Tek (Sakura Finetek Japan), and frozen in liquid nitrogen to prepare a cross-sectional frozen section having a thickness of 5 The frozen section was permeabilized with 100% methanol for 30 minutes at −20° C., blocked with PBS+0.2% TritonX+5% bovine serum albumin, and then reacted overnight at 4° C. with an anti-NF200 rabbit antibody (1:1000; 102M4784; Sigma-Aldrich Co. LLC.) and an anti-MBP mouse antibody (1:1000; NE1018; Calbiochem) as primary antibodies. The reacted section was reacted for 1 hour with Alexa 488-labeled goat anti-rabbit IgG antibody (1:1000; Lifetechnologies) and Alexa 568-labeled goat anti-mouse IgG antibody (1:1000; Lifetechnologies) as secondary antibodies. After the secondary antibody reaction, the section was reacted with a mounting medium (product name: Perma fluor [registered trademark]; Thermo Fisher Scientific) containing DAPI (4'-6-diamidinophenyl-2-indole; Wako Pure Chemical Corporation) to evaluate nuclei. A ratio of (the number of MBP positive axons)/(the number of total axons) was calculated as a ratio of myelinated axons (mean±standard error) by using NIS Elements BR software (Nikon Corporation), and the ratio was evaluated. Examples of results of the above test are shown in Table 15.

TABLE 15

| | The Ratio of myelinated axons (%) |
|---|---|
| Onset Control | 67.1 ± 1.5 |
| Present Extract Administration | 79.9 ± 1.1*** |

***$p < 0.001$ vs Onset Control

As compared with the onset control group, the ratio of myelinated axons increased significantly in the present extract administration group, and thus the myelination promoting action was confirmed (Table 15).

Test Example 7: Evaluation in Rat Sciatic Nerve Local Demyelination Model

Using an LPC-induced demyelination model, effects of the present extract on remyelination after demyelination were investigated. In the same manner as in the above Test example 6 (1), the present extract was continuously administered to rats by using an osmotic pump, and the immunohistological evaluation was conducted.

(1) Preparation of Sciatic Nerve Local Demyelination Model Rats and Administration of Present Extract In the same manner as in Test example 6, an osmotic pump (product name: alzet [registered trademark], model: 2ML1, product of DURECT) was filled with saline or the present extract, and stood still overnight in saline at 37° C. Male Wistar rats aged 6 weeks were deeply anesthetized using intraperitoneal administration of a mixed anesthetic of midazolam (2 mg/kg), butorphanol (2.5 mg/kg), and medetomidine (0.15 mg/kg). The left sciatic nerve was exposed in a sciatic notch level, and 5 µL each of saline or 2% LPC (Sigma-Aldrich) was administered to a proximal sciatic nerve with the use of a Hamilton syringe. After 7 days from administration of LPC, either a saline-filled osmotic pump or a present extract-filled osmotic pump (24 NU/kg/day) was placed subcutaneously in the back of rats, and saline or the present extract was continuously administered for the following one week.

(2) Immunohistological Evaluation

Rats after a lapse of 2 weeks from the operation were sedated with an anesthetic, and sciatic nerves were sampled. In the same manner as in the above Test example 6 (2), a ratio of (the number of MBP positive axons)/(the number of total axons) was calculated as a ratio of myelinated axons (mean±standard error) by using NIS Elements BR software (Nikon Corporation), and the ratio was evaluated. Examples of results of the above test are shown in Table 16.

TABLE 16

| | The Ratio of myelinated axons (%) |
|---|---|
| Onset Control | 41.4 ± 0.58 |
| Present Extract Administration | 74.4 ± 0.46*** |

***$p < 0.001$ vs Onset Control

As compared with the onset control group, the ratio of myelinated axons increased significantly in the present extract administration group, and thus the promotion of myelination was confirmed (Table 16).

(3) Evaluation of Sciatic Function Index

To evaluate the motor function, a sciatic function index (SFI) was measured 2 weeks after the operation. For measurement of SFI, ink was applied to the soles of hind paws of rats, and office paper was placed on a level pedestal of 40 cm-square, and rats were allowed to walk on the office paper and the footprints were recorded. The following parameters were measured, and SFI was calculated according to the following formula. SFI=0 indicates normal, and SFI=−100 indicates complete loss of function. An individual in which necrosis or defect occurred in the paw during the postoperative course was excluded.

$$SFI = -38.3 \times ((EPL-NPL)/NPL) + 109.5 \times ((ETS-NTS)/NTS) + 13.3 \times ((EITS-NITS)/NITS) - 8.8 \text{<SFI Numerical Formula>}$$

<each item>
EPL=experimental print length
NPL=normal print length
ETS=experimental toe spread
NTS=normal toe spread
EITS=experimental intermediary toe spread
NITS=normal intermediary toe spread One example of the result of the above test is shown in Table 17.

TABLE 17

| | Sciatic Functional Index (%) |
|---|---|
| Control | −9.25 ± 0.99 |
| Present Extract Administration | −7.66 ± 1.18 |
| Onset Control | −22.5 ± 3.13*** |
| Onset Present Extract Administration | −7.75 ± 0.41### |

***$p < 0.001$ vs Control,
$p < 0.001$ vs Onset Control

As compared with the onset control group, SFI recovered significantly in the present extract administration group, and thus the motor function was ameliorated (Table 17).

(4) Von Frey Test

To evaluate the sensory function, at 2 weeks after the operation, hind paw withdrawal thresholds to mechanical stimuli (mechanical hind paw withdrawal thresholds) were measured by using von Frey filaments (0.008 g to 26 g, product name: TouchTest [registered trademark]; North Coast Medical). A rat was allowed to walk on a mesh fence, and a pressure was applied on the plantar surface with the filaments, and a value at which the rat showed an avoiding reaction was recorded. For evaluation, measurement was conducted on each of the unaffected side and the affected side, and the ratio of (a value in the affected side)/(a value in the unaffected side) was calculated and evaluated. Examples of results of the above test are shown in Table 18.

TABLE 18

| | Paw with drawal threshold affected side/unaffected side |
|---|---|
| Control | 0.89 ± 0.08 |
| Present Extract Administration | 0.88 ± 0.06 |
| Onset Control | 1.65 ± 0.30* |
| Onset Present Extract Administration | 0.83 ± 0.08## |

*$p < 0.05$ vs Control
$p < 0.01$ vs Onset Control

As compared with the onset control group, the ratio of (the value in the affected side)/(the value in the unaffected side) of hind paw withdrawal thresholds to mechanical stimuli (mechanical hind paw withdrawal thresholds), which is a functional evaluation of a sensory nerve, recovered significantly in the onset present extract administration group, and thus paresthesia (hypesthesia) was ameliorated (Table 18).

(5) Hot Plate Test

To evaluate the response to a thermal stimulus, at 2 weeks after the operation, the time until the animal shows the first avoiding reaction of the affected paw (licking or raising the affected paw) (Hot plate latency) was measured at a setting of 52.5° C. by using a hot plate device (Ugo basile). The cutoff time was 45 seconds. Examples of results of the above test are shown in Table 19.

TABLE 19

| | Hot Plate Latency (s) |
|---|---|
| Control | 10.1 ± 0.54 |
| Present Extract Administration | 9.20 ± 0.43 |
| Onset Control | 13.6 ± 0.43*** |
| Onset Present Extract Administration | 9.57 ± 0.57### |

***$p < 0.001$ vs Control,
$p < 0.001$ vs Onset Control

In the hot plate test, significant improvement was observed and the thermal paresthesia (hypesthesia) ameliorated in the present extract administration group compared with the onset control group (Table 19).

(6) Electrophysiological Evaluation

A rat after a lapse of 2 weeks from the operation was sedated with an anesthetic, and placed in the prone position on the operating table. The left sciatic nerve and the left tibialis anterior muscle were exposed. Stimuli were applied on the proximal side and the distal side of the sciatic nerve crush injury site with a bipolar electrode, and a nerve conduction velocity (NCV) was calculated from the respective measurements. Stimuli were applied on the proximal side of the sciatic nerve with a bipolar electrode, and terminal latency (TL) and a compound muscle action potential (CMAP) were measured. For measurement and evaluation, a data recording and analyzing system PowerLab 2/26 (AD Instruments) was used. Examples of results of the above test are shown in Table 20 to Table 22.

TABLE 20

| | Nerve Conduction Velocity (m/s) |
|---|---|
| Control | 41.8 ± 2.230 |
| Present Extract Administration | 40.7 ± 2.01 |
| Onset Control | 23.8 ± 2.02*** |
| Onset Present Extract Administration | 41.3 ± 1.46### |

***$p < 0.001$ vs Control,
$p < 0.001$ vs Onset Control

TABLE 21

| | Terminal Latency (ms) |
|---|---|
| Control | 1.84 ± 0.06 |
| Present Extract Administration | 1.89 ± 0.05 |
| Onset Control | 2.43 ± 0.12*** |
| Onset Present Extract Administration | 1.88 ± 0.04### |

***$p < 0.001$ vs Control,
$p < 0.001$ vs Onset Control

TABLE 22

| | CMAP (mV) |
|---|---|
| Control | 48.0 ± 3.61 |
| Present Extract Administration | 48.1 ± 4.42 |
| Onset Control | 25.2 ± 5.07* |
| Onset Present Extract Administration | 47.3 ± 5.13# |

***$p < 0.001$ vs Control,
$p < 0.001$ vs Onset Control

As compared with the onset control group, NCV, TL, and CMAP recovered significantly in the present extract administration group, and thus the electrophysiological function was ameliorated (Table 20 to Table 22).

From the foregoing, preferred embodiments of the present invention include the following. However, it is to be noted that the present invention is not limited to these embodiments.

(1) An agent for promoting differentiation of Schwann cells containing an extract from inflamed tissues inoculated with vaccinia virus.
(2) The agent for promoting differentiation of Schwann cells according to (1), wherein the agent is an agent for promoting peripheral nerve regeneration.
(3) The agent for promoting differentiation of Schwann cells according to (2), wherein the agent for promoting peripheral nerve regeneration is an agent for treating peripheral nerve injury.
(4) The agent for promoting differentiation of Schwann cells according to (2), wherein the agent for promoting peripheral nerve regeneration is an agent for treating demyelinating disease.
(5) The agent for promoting differentiation of Schwann cells according to any one of (1) to (4), wherein the promotion of differentiation is promotion of myelination.
(6) The agent for promoting differentiation of Schwann cells according to (5), wherein the promotion of myelination is promotion of expression of a myelin sheath-associated protein.
(7) The agent for promoting differentiation of Schwann cells according to (6), wherein the myelin sheath-associated protein is MBP, P0, PMP22, or periaxin.
(8) The agent for promoting differentiation of Schwann cells according to any one of (1) to (7), wherein the inflamed tissues are inflamed skin tissues of rabbits.
(9) The agent for promoting differentiation of Schwann cells agent according to any one of (1) to (8), wherein the agent is an injection preparation.
(10) The agent for promoting differentiation of Schwann cells according to any one of (1) to (8), wherein the agent is an oral preparation.
(11) A determining or evaluating method for an extract from inflamed tissues inoculated with vaccinia virus or a preparation containing the extract, wherein an action to the expression of a myelin sheath-associated protein in Schwann cells is used as an index.
(12) The determining or evaluating method according to (11), wherein the myelin sheath-associated protein is MBP, P0, PMP22, or periaxin.
(13) The determining or evaluating method according to (11) or (12), wherein the action to the expression of a myelin sheath-associated protein is a promoting action.
(14) The determining or evaluating method according to any one of (11) to (13), wherein the action to the expression of a myelin sheath-associated protein is measured by using an action to a MEK/ERK pathway protein of a cell as an index.
(15) The determining or evaluating method according to (14), wherein the MEK/ERK pathway protein is ERK1/2.
(16) The determining or evaluating method according to (14) or (15), wherein the action to the MEK/ERK pathway protein is a protein-phosphorylation inhibitory action.
(17) The determining or evaluating method according to any one of (11) to (13), wherein the action to the expression of a myelin sheath-associated protein is measured by using an action to a PI3K/AKT pathway protein of a cell as an index.
(18) The determining or evaluating method according to (17), wherein the PI3K/AKT pathway protein is AKT.
(19) The determining or evaluating method according to (17) or (18), wherein the action to the PI3K/AKT pathway protein is a protein-phosphorylation promoting action.
(20) The determining or evaluating method according to any one of (11) to (19), wherein the inflamed tissues are inflamed skin tissues of rabbits.
(21) A method for verifying that an extract from inflamed tissues inoculated with vaccinia virus or a preparation containing the extract satisfies the quality standard by performing the determination or evaluation as described in any one of (11) to (20).
(22) The method according to (21), wherein the preparation containing an extract from inflamed tissues inoculated with vaccinia virus is an injection preparation or an oral preparation.
(23) A method for treating a peripheral nerve injury, comprising administering an extract from inflamed tissues inoculated with vaccinia virus or a preparation containing the extract to a patient in need of the treatment.
(24) The method according to (23), wherein the treatment of a peripheral nerve injury is promotion of differentiation of Schwann cells.
(25) A method for treating a demyelinating disease, comprising administering an extract from inflamed tissues inoculated with vaccinia virus or a preparation containing the extract to a patient in need of the treatment.
(26) The method according to (25), wherein the treatment of demyelinating disease is a treatment by promotion of differentiation of Schwann cells.
(27) The method according to (24) or (26), wherein the promotion of differentiation is promotion of myelination.
(28) The method according to (27), wherein the promotion of myelination is promotion of expression of a myelin sheath-associated protein.
(29) The method according to (28), wherein the myelin sheath-associated protein is MBP, P0, PMP22, or periaxin.
(30) The method according to any one of (23) to (29), wherein the inflamed tissues are skin tissues of rabbits.
(31) The method according to any one of (23) to (30), wherein the administration is performed by injection.
(32) The method according to any one of (23) to (30), wherein the administration is performed by oral administration.

INDUSTRIAL APPLICABILITY

As described above, the present extract shows a Schwann cell differentiation promoting action and a peripheral nerve regeneration promoting action. Thus, it is thought that a preparation containing the present extract has a therapeutic effect on a peripheral nerve injury.

The invention claimed is:

1. A method for promoting differentiation of Schwann cells, comprising administering an agent containing an extract from inflamed tissues inoculated with vaccinia virus to a subject in need thereof to treat demyelinating disease of a peripheral nerve in the subject.

2. The method according to claim 1, wherein the agent is administered to treat peripheral nerve injury in the subject.

3. The method according to claim 1, wherein the promotion of differentiation is promotion of myelination.

4. The method according to claim 3, wherein the promotion of myelination is promotion of expression of a myelin sheath-associated protein.

5. The method according to claim 4, wherein the myelin sheath-associated protein is MBP, P0, PMP22, or periaxin.

6. The method according to claim 1, wherein the inflamed tissues are inflamed skin tissues of rabbits.

7. The method according to claim 1, wherein the agent is administered to the subject by injection.

8. The method according to claim 1, wherein the agent is orally administered to the subject.

* * * * *